United States Patent [19]
Worthington et al.

[11] Patent Number: 5,987,990
[45] Date of Patent: Nov. 23, 1999

[54] SYSTEM OF AUTONOMOUS SENSORS FOR PIPELINE INSPECTION

[75] Inventors: Henry W. Worthington; Loren K. Worthington, both of Scottsdale, Ariz.

[73] Assignee: Pipeline Technologies, Inc., Scottsdale, Ariz.

[21] Appl. No.: 08/963,869

[22] Filed: Nov. 4, 1997

Related U.S. Application Data

[60] Provisional application No. 60/046,301, May 13, 1997.
[51] Int. Cl.⁶ .................................................... G01N 29/04
[52] U.S. Cl. .......................... 73/592; 73/594; 73/40.5 A; 73/579
[58] Field of Search ...................... 73/592, 587, 40.5 A, 73/594, 579

[56] References Cited

U.S. PATENT DOCUMENTS

| | | |
|---|---|---|
| 4,083,229 | 4/1978 | Anway . |
| 4,289,019 | 9/1981 | Claytor ................................. 73/40.5 A |
| 4,459,851 | 7/1984 | Crostack ................................... 73/587 |
| 4,549,437 | 10/1985 | Weins et al. ............................. 73/587 |
| 4,858,462 | 8/1989 | Coulter et al. ........................ 73/40.5 A |
| 4,901,575 | 2/1990 | Bohannan et al. ........................ 73/487 |
| 4,956,999 | 9/1990 | Bohannan et al. ........................ 73/587 |
| 5,117,676 | 6/1992 | Chang . |
| 5,255,565 | 10/1993 | Judd et al. ................................ 73/579 |
| 5,333,501 | 8/1994 | Okada et al. . |
| 5,456,113 | 10/1995 | Kwun et al. .............................. 73/587 |
| 5,457,994 | 10/1995 | Kwun et al. .............................. 73/587 |
| 5,540,096 | 7/1996 | Woodcock et al. ....................... 72/579 |
| 5,739,420 | 4/1998 | Peterson ............................... 73/40.5 R |

OTHER PUBLICATIONS

Suprenant, B.A., et al., "Nondestructive evaluation of Civil Structures and Materials", May 1992, pp. 427–453.
Travers, Fred "Acoustic Monitoring of Prestressed concrete Pipe at the Agua Fria River Siphon, "Bureau of Reclamation Fimal Report, Dec. 1994.

*Primary Examiner*—Hezron Williams
*Assistant Examiner*—Rose M. Miller
*Attorney, Agent, or Firm*—James C. Wray; Meera P. Narasimhan

[57] ABSTRACT

A flaw detection system for a prestressed concrete cylinder pipe uses hydrophones inserted into valves in the pipe while the pipe is in use. The hydrophones listen for sounds that are consistent with the breaking of the pre-tensioned reinforcements and the sliding and re-anchoring of broken ends. Detecting the sound at two or more locations and establishing precise time differentiation allows the precise calculation of the location of the defect. Global positioning system (GPS) satellite receivers provide precise timing of reception of the targeted sound events in milliseconds. The location of each of the hydrophones is established using GPS. Each hydrophone is connected to a box, which includes a pre-amplifier, a signal processor, a memory, an output and a GPS receiver. The hydrophone, or box, or both, are tunes to recognize a significant sound that emanates from a breaking, moving or re-anchoring reinforcement. The precise time of arrival of that sound is recorded in the boxes using the GPS time signals. The sound wave information may also be recorded, as well as water temperature, pressure and velocity. Later the precise time and sound wave data is collected from the memories in the boxes and is compared with time and sound wave data from the memories and other boxes. Time differentials are used to determine the precise location of the source of the sound along the pipeline.

31 Claims, 3 Drawing Sheets

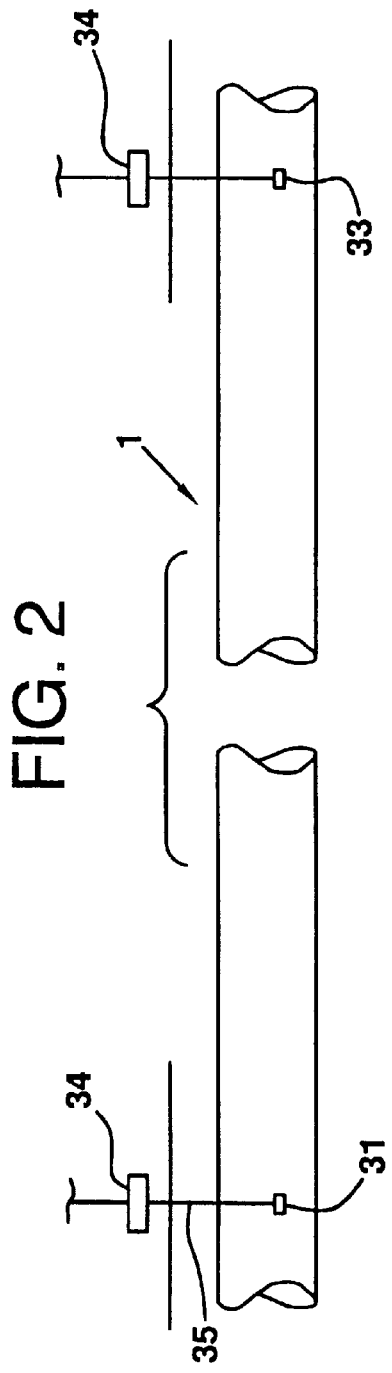
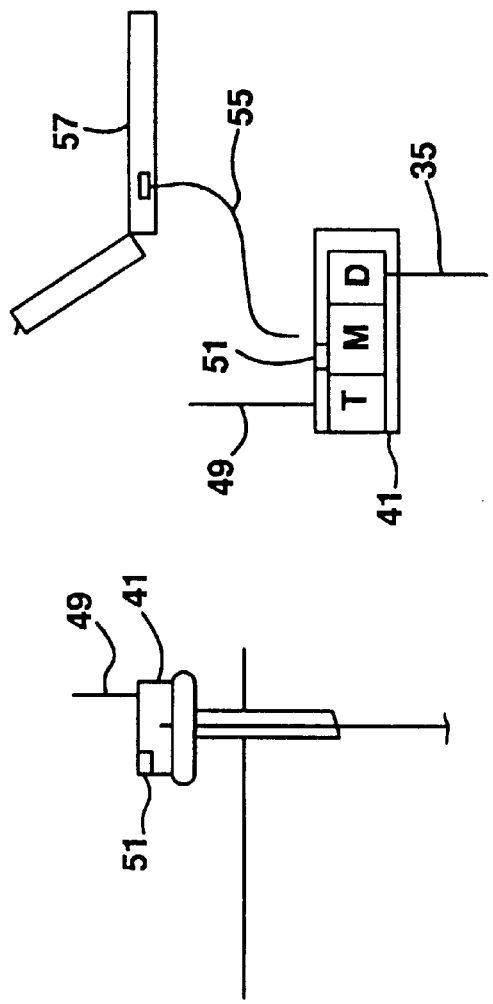
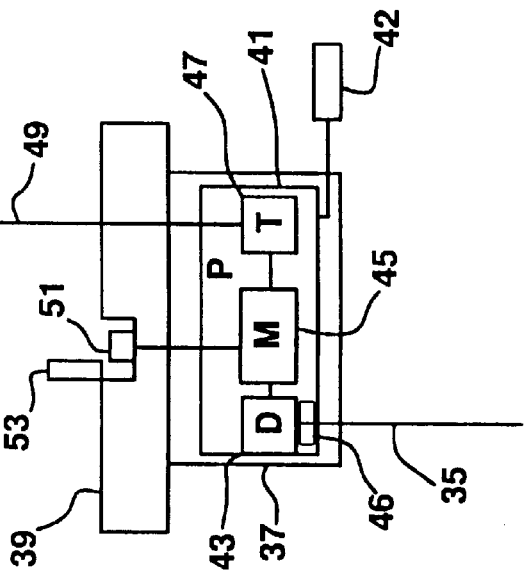

SYSTEM OF AUTONOMOUS SENSORS FOR PIPELINE INSPECTION

This application claims the benefit of U.S. provisional application No. 60/046,301, filed May 13, 1997.

SUMMARY OF THE INVENTION

The present invention provides a system of autonomous sensors for the inspection of pipelines, bridges, buildings and other structures. As used herein the term "AH-1" refers to the entire system which includes the following components: sensors, pre-amplifiers, remote acoustic signal processors and central acoustic signal processors.

In the preferred embodiment, the sensors are hydrophones and the terms "sensors" and "hydrophones" are interchangeable.

The signals produced by each sensor are amplified before further processing by a device referred to as a pre-amplifier, or "preamp". In some instances the sensor is assembled with an embedded signal pre-amplifier, and in other cases it is a separate component. A remote acoustic signal processor (RASP) component is referred to herein as the "signal detector/recorder". It includes the GPS signal receiver, the acoustic signal detector, and the digital memory. The central acoustic signal processor (CASP) is called the signal analyzer in the body of the disclosure.

The disclosure includes all structures, pipelines, materials and fluids. The concept of time-tagged acoustic signal inspection may be applied to any other type of structure. The invention covers all civil structures such as bridges, stadiums and buildings.

An example of the system is described for prestressed concrete pipes. The invention is useful with other pipe materials and other types of structures.

The sensors may also include water pressure, water temperature and water velocity sensors.

There will be other sensor types in the future. The inventors have experimented with accelerometers with some success.

There may be other types of clocks, timers or time tagging devices in the future which would be more appropriate. For now the GPS is the best mode contemplated at the time of filing the application.

Recorded data consists of precise time and sound. The invention records the time of arrival of the acoustic transient at hydrophone #1, in seconds, with an accuracy of ±0.0001 seconds and the time of arrival of the acoustic transient at hydrophone #2, in seconds, with an accuracy of ±0.0001 seconds. The invention samples recorded data with a laptop computer or uses a portable hard drive to transfer data from the RASP to the CASP. There will undoubtedly be other data transfer schemes in the future.

An important aspect of the invention is that a transient or sound associated with an indicator of deterioration is precisely timed at its location of reception. The sound or transient is recorded with a precise time tag from a GPS receiver.

The autonomous hydrophone, pickup or sensor (hereafter referred to as the AH1) is a method of non-destructive testing which identifies and localizes deterioration of pipelines. It uses a series of sensors placed in or on pipelines which detect and record acoustic emissions of distress, and which also incorporate an accurate clock or timing system. The precise instant of the detection is recorded simultaneously by reception of the acoustic emission itself. The data thus collected is used to classify the acoustic emission as to the nature and location of its source. Structural deterioration is identified in those instances when the signature of the emission matches the known emission of deterioration. Localization of the source is established based on the difference in the time of signal detection at two or more sensors, the known location of those sensors and the speed of sound in the particular medium.

The AH1 is distinct from prior uses of acoustic emission detection systems in important respects. Prior uses transmitted acoustic signals from the series of sensors to a single recorder. In prior uses, the real-time transmission of signals provided a means of determining the difference in the time of signal detection at the various sensors. That information in turn could be used to localize the source of the signal. The telemetry system required for signal transmission consisted of wire or fiber cables, or a radio frequency transmitter/receiver system. Logistical barriers to establishing these telemetry systems have limited the practical application of the technology. The new AH1 system eliminates the telemetry system altogether by recording the acoustic data and the precise timing of detection at the hydrophone. The AH1 accomplishes the same function as prior uses of acoustic emission detection systems used in non-destructive testing, i.e. the localization and classification of emissions emanating from points of distress within pipelines.

The invention is a flaw detection system for a prestressed concrete cylinder pipe in which hydrophones are inserted into valves in the pipe while the pipe is in use. The hydrophones listen for sounds which are consistent with the breaking of the pre-tensioned reinforcements. Detecting the sound at two or more locations and establishing precise time differentiation allows the precise prediction of the location of the source of the sound. Wiring distant hydrophones to an analyzer has been the previous approach. That has been unsatisfactory because of the great distance between the signal processors and hydrophones.

The invention uses the global positioning system GPS satellites for precise timing of events in milliseconds. The location of hydrophones is established using GPS. The system works with two or more hydrophones. Each hydrophone is connected to a box. The hydrophone or box, or both, are tuned to recognize a significant sound that emanates from a breaking or moving reinforcement. The precise time of arrival of that sound is recorded in the boxes using the GPS time signals. The sound wave information may also be recorded. Later the precise time and sound wave data is collected from the memories in the boxes and compared with time and sound wave data from the memories and other boxes, and time differentials are used to determine the precise location of the source of the sound along the pipeline.

The AH1 system is designed for use on prestressed concrete water pipelines (PCCP). Typical new systems for use on different types of structures include the following components:

(a) Sensors: The AH1 uses a series of two or more sensors or pickups, for example, in the form of hydrophones placed through the walls of the pipe and into the column of water. These hydrophones are placed at intervals of up to 2500 feet using presently available sensors. The hydrophones have a continuous range of sensitivity from 0 to more than 20 kHz. An analog electric potential is produced by the hydrophone. It is transmitted via metallic wire to a signal processor on the exterior of the pipe. The sensors, interval between sensors and method of installing in or on the pipeline or on other structures may be tailored to specific requirements. In prestressed concrete water pipes, the sound of distress will most commonly be an emission from the prestressing wire. PCCP is manufactured with prestressing wire helically wrapped with tension of up to 8000 pounds (see FIG. 1). The concrete core is thus placed in compression, and the pipe is structurally capable of withstanding the forces caused by the water pressure and the weight of the concrete, soil and water. The prestressing wire is covered by a thin layer of mortar for protection. When distress occurs, it involves the prestressing wire. The resulting corrosion or embrittlement or cracking reduces the load-carrying capability of the prestressing wire. That causes the wire to break. The break results in energy release, some of which is in the form of acoustic energy which is propagated through the wall of the pipe and into the column of water within the pipe. The wire tends to re-anchor within a few wire diameters. If deterioration of that wire continues, it results in many additional breakages and energy releases. Each energy release propagates a transient acoustic signal through the pipe. The hydrophones detect those acoustic transients.

(b) Millisecond-accuracy clock: A global position satellite system (GPS) receiver is co-located with each hydrophone at the data sampling site. The GPS signal provides the means for determining the precise time of detection of an acoustic transient to an accuracy of within one microsecond. It also provides information as to the exact location of the hydrophone. That data is transmitted continuously or periodically to the signal detector/recorder.

(c) Signal detector/recorder: The signal detector/recorder is a digital computer which is housed in a rugged, all-weather case and is co-located with each hydrophone at the data sampling site. The detector/recorder digitizes and continuously analyzes the acoustic noise detected by the hydrophone. Software within the signal detector/recorder identifies transient signals and compares all transient signals detected against parameters established by the system's human operator. As a minimum, the signal strength and duration of transient signals is measured and compared to threshold settings. When a signal meets the thresholds established, a detection is declared by the signal detector/recorder. At that time the digitized signal and the time of detection are recorded in an electronic file. The electronic file is stored in a memory within the local digital computer. A file includes a time-series representation of the transient, including:

the digitized data, the chronological time at one or more points on the time scale to an accuracy of at least 0.1 milliseconds and the location of the hydrophone at the time of the detection.

After establishing the file, the system continues to monitor incoming signals until deactivated by the operator. Data files are transferred manually or electronically from the signal detector/recorder for further interpretation by a signal analyzer. The signal detector/recorder, sample rates, degree of resolution and other characteristics of signal storage are tailored to the installation accessibility and staff availability. Data of time and sound or time, sound and location are stored at the detector/recorder. A worker may visit an accessible site and take information from each detector/recorder, such as by connecting the detector/recorder with a laptop or notebook computer or otherwise transferring records, such as by keying entry or infrared scanning or transmission.

Each detector/recorder may have a transmitter which gives its ID and recent data continuously, periodically or upon receiving a request for data.

(d) Signal analyzer: The signal analyzer is a digital computer which receives and interprets data from a series of two or more signal detector/recorders. The signal analyzer analyzes the data files in the following manner. Data regarding the physical characteristics of the structure is stored in the signal analyzer. That data includes dimensions and configurations of the structure, and the speed of sound propagation in the media within the structure. Data regarding the location of each of the sensors obtained empirically or from the GPS is stored in the signal analyzer. That includes the acoustic distance between the sensors and the latitude and longitude of the sensors.

The data files from each of the detector/recorders are transferred to the signal analyzer.

All data files are further classified by a signal processing software package. Those matching the acoustic signature of structural deterioration are identified as such. Those signals not matching the acoustic signature of interest are classified as to their nature if possible, or identified as unknown for disposition by the human operator. The signal analyzer has the capability to do extensive signal analysis, including audio reproduction, and graphic and numeric analysis of the acoustic signal.

Upon each signal identified as deterioration-related, the signals from adjacent hydrophones are screened to determine whether that transient was detected within the signal-travel-time of the first. If there is a plausible detection of the same signal between two adjacent hydrophones, the location of the origin of the signal will be determined by the formula:

$$X = (V(T1-T2)+d) \div 2$$

Where $X$=the distance of the point of structural distress from hydrophone #1, in feet;

$V$=the velocity of sound propagation in the liquid within the pipe, in feet per second;

$T1$ and $T2$=the time of arrival of the acoustic transient at hydrophones 1 and 2, in seconds, with an accuracy of $\pm 0.0001$ seconds;

$d$=the total distance between hydrophones in feet, measured along the line the transient signal will follow within the structure.

That formula is modified to account for the speed of the fluid within the pipeline in those instances where that significantly affects localization of the source of the transient.

All data from all hydrophones is similarly analyzed, and the results are depicted numerically and graphically.

In that way the location of points of deterioration are determined, and the purpose of the invention is performed. This non-destructive testing normally is accomplished while the pipe remains in full operation.

The software may be replaced with amplifiers and filters for detecting signals in known frequency ranges.

The inventors have successfully inspected a concrete pipeline in search of cracks and flaws in a unique fashion. This method entailed the manipulation of the pressure within the pipeline to induce acoustic emissions by cracks or other anomalies within the structure of the pipe. The new AH-1 system successfully recorded acoustic transients in the pipeline.

BRIEF DESCRIPTION OF THE DRAWINGS

FIG. 2 is a schematic representation of a pipeline with hydrophones installed.

FIG. 3 is a schematic representation of an on-board digital computer installed at each hydrophone.

FIG. 4 is a schematic representation of a digital computer installed above the ground at each hydrophone.

FIG. 5 is a schematic representation of a laptop computer receiving data from a memory of an individual digital computer.

DETAILED DESCRIPTION OF THE PREFERRED EMBODIMENTS

Figure 1:
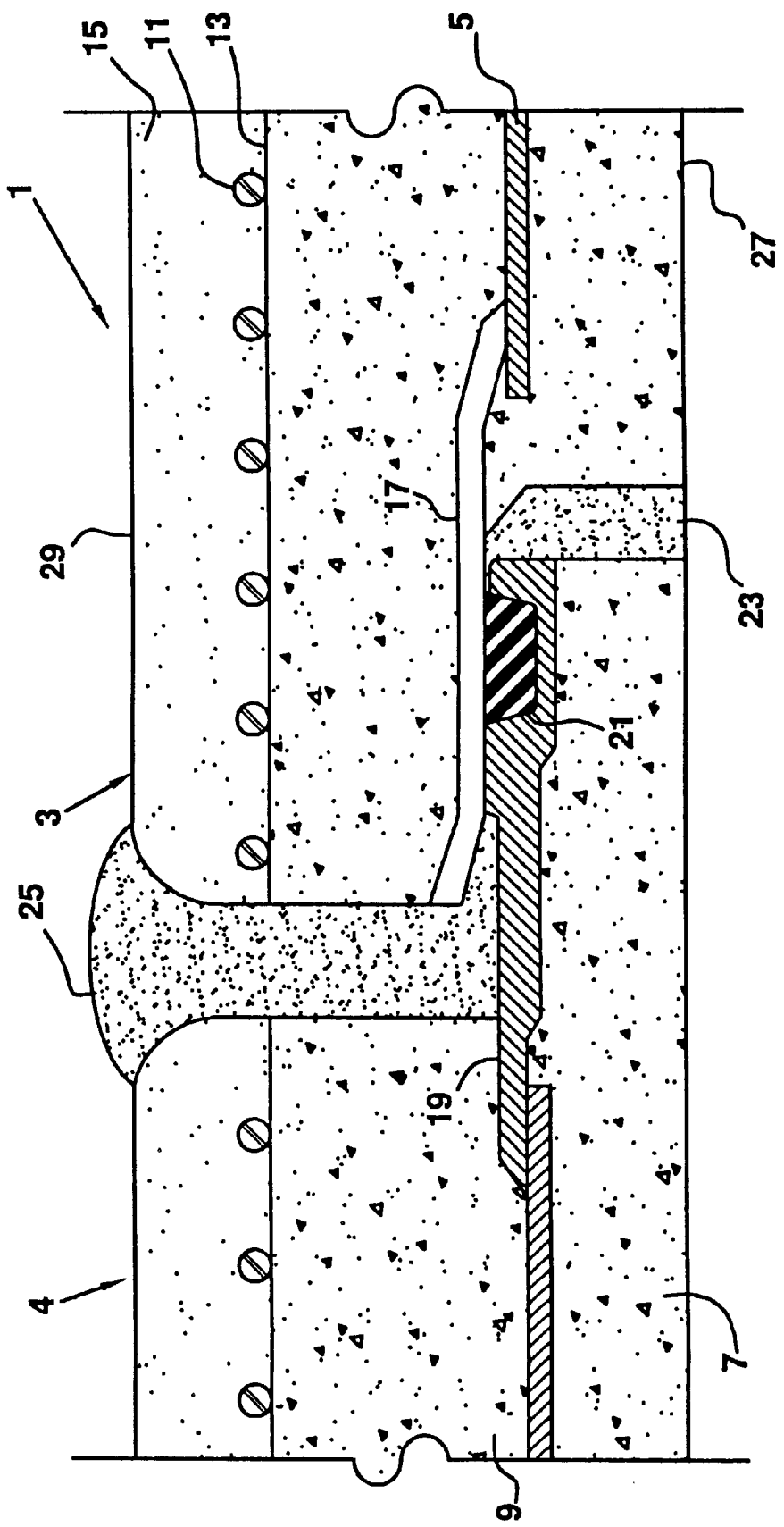
FIG. 1 is a cross-section of prestressed concrete pipe.

Referring to FIG. 1, a prestressed concrete pipe, generally indicated by the numeral 1, is shown in quarter section at a bell 3 and spigot 4 connection. The pipe has a steel cylinder 5 surrounded by an inner 7 and outer 9 concrete core. Prestressed wire 11 is wound around the outer surface 13 of the outer concrete core 9, which hold the pipe in compression. A layer 15 of cement or mortar coating covers the prestressed wires 11. The sound of failure of the prestressed wire is what is used to trigger the sound and time recordings in the memory of the present invention.

The prestressed cylinder bell has a steel bell ring 17 welded to an end of the steel cylinder and a steel spigot ring 19 welded to an end of the steel cylinder. Before the pipes are pushed together, an elastomeric gasket 21 is placed in a groove near the end of the steel spigot ring 19. The pipes, which are typically 36 inches to 15 feet in diameter, are shoved together. The voids in the joint are filled with grout externally 25 and internally 23 protect the gasket 21. Water flows along the inner surface 27 of the pipe. The outer surface 29 of the pipe is covered with backfill. The pipes normally continue in use for many years without problems. When problems do occur, they may be because of cracking of the cement mortar coating, which allows moisture to degrade part of the prestressed wire 11. Since the wire remains under tension, sufficient degradation causes the wire to snap. It is the sound of the snapping and subsequent slippage of the prestressed wire that is conveyed through the water and picked up by the hydrophones 31 and 33 shown schematically in the pipeline 1 in FIG. 2. Pre-amplifiers 34 may be connected to the hydrophones for pre-amplifying signals supplied through signal wires 35 to the signal processor.

In the invention, the hydrophones are autonomous and are not connected to other hydrophones.

As shown in FIG. 3, the signal wires 35 from the hydrophones lead upward to a box 37 with a cover plate 39 at ground level. A digital processor P indicated by the numeral 41 is positioned within the box. The processor has a detector 43, a memory 45 and a precision timer 47, noise filter 46 comprising high and low band pass filters. A power source 42 may be connected to the processor. The timer has an antenna 49 for receiving precise time signals from a GPS satellite. When the snapping of a prestressed wire or the grinding noises associated with movement and re-anchoring of broken ends of the wire are sensed by the detector 43, the information is provided to the memory 45, which concurrently receives precise time information from timer 47. All of that data is stored in the memory 45 until the data is accessed through a data port 51, which is schematically shown as being accessed through a hatch 53 in the cover 39.

FIG. 4 shows an alternate form of the invention in which a digital computer 41 is mounted on an above ground pipeline support unit, for example a control valve, which extends above the ground. The self-contained digital computer 41 has an antenna 49 and a data port 51.

As schematically shown in FIG. 5, a digital processor 41, which is connected by a wire 35 to a hydrophone, has a data port 51 and an antenna 49. The data port 51 is accessed by a connector 55 or an infrared sensor, which is connected to a laptop computer 57. When it is desired to collect data from the individual units, a person visits each unit to collect the data has been accumulated. Later a comparison of the precise GPS time of each event provides pinpointing of the location of the prestressed wire rupture or grinding event.

Figure 6:
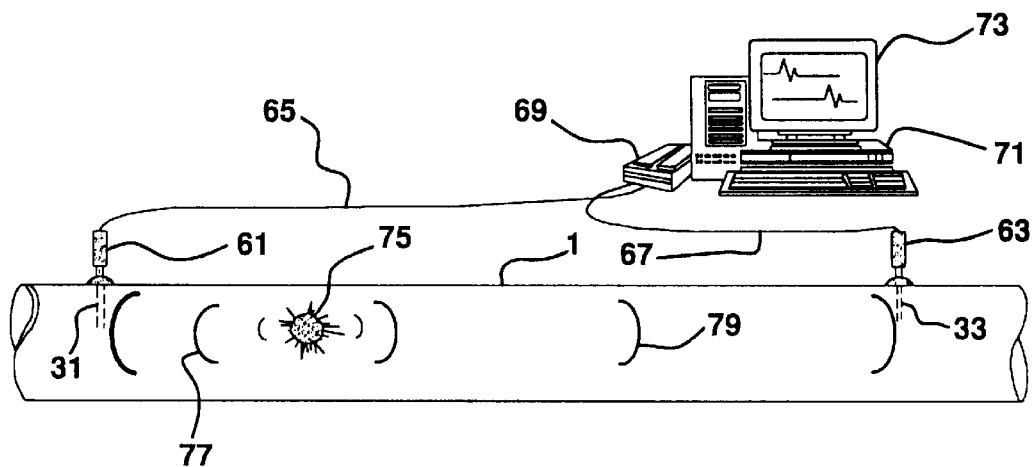
FIG. 6 is a schematic representation of existing wired technology.

FIG. 6 is a schematic representation of an existing wired technology. Hydrophones 31 and 33 are mounted in a pipe 1 with hydrophone mounts 61 and 63. The hydrophone mounts are connected to a central processor via communication links 65 and 67, which lead to a modem 69. A central processor 71 with a monitor 73 reveals the location of an incident 75 by virtue of the time of arrival of sound waves 77 and 79 at hydrophones 31 and 33. The direct communication links 65 and 67 introduce problems and are difficult to connect and maintain due to the long distances between hydrophones 31 and 33.

Figure 7:
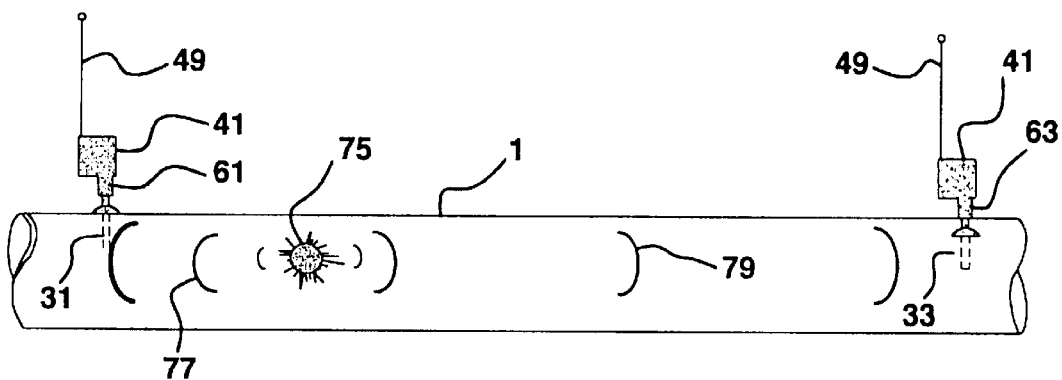
FIG. 7 is a schematic representation of new wireless GPS technology.

As shown in FIG. 7, the hydrophone mounts 61 and 63 of the present invention support processors 41, which include GPS receivers connected to antennas 49.

Data is stored in memories in the processors 41 and is transferred from the processors, as shown schematically in FIG. 5, by inputting the stored information to a laptop computer 57. The processor records the sound received by the hydrophone, the precise time of arrival of that sound, and the specific position of the hydrophone. The precise time and the position of the hydrophone mount are provided by the GPS receiver co-located with each GPS receiver within the processor 41.

Figure 8:
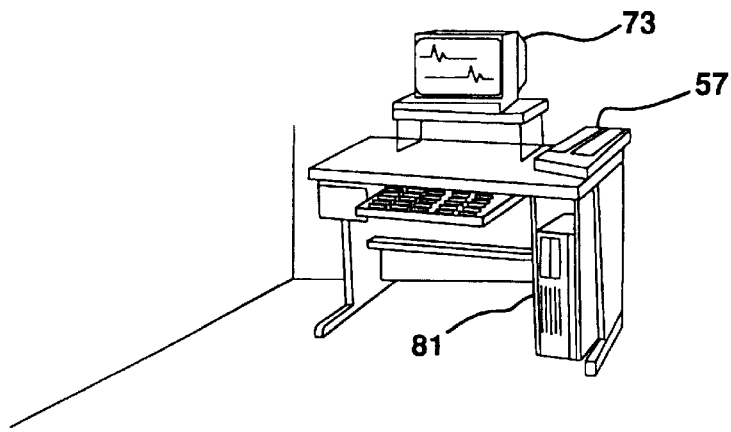
FIG. 8 is a schematic representation of a central station.

As shown in FIG. 8, the laptop computer 57 is taken to the central processing station and connected to the central acoustic signal processor 81, where it provides information of the signal characteristic,.the precise times of arrival, and the locations of the hydrophones.

A pipeline flaw detection system for a prestressed concrete cylinder pipe has plural pickup units. Each unit has a pickup for mounting in or connecting to the pipe and has a memory connected to the pickup for recording significant wave energy from the pickup. Each unit has a global positioning system antenna, a receiver connected to the antenna and a time signal extractor connected to the receiver for extracting a time signal from the receiver. The receiver is connected to the memory for recording the time signal with the significant wave energy in the memory. An output connected to the memory provides an output of significant wave data, the precise time signal and the location of the processor 41.

A computer receives information from the outputs of the pickup units one-by-one and compares sound signals, hydrophone locations and times, providing time differentiation and predicting position of a flaw in the pipe.

Other structure types have different emissions caused by different events. Reinforcing steel in other post-tensioned and prestressed concrete structures (such as buildings and bridges) have emissions caused by the deterioration or relaxation of the reinforcement. Steel cables in suspension bridges cause emissions with the loss of any strands in the cables. In the instance of steel pipelines, it is possible to induce an anomalous pattern of emissions from areas of structural distress by changing the pressure of the fluid within the pipe. In the instance of steel structures, it is possible to induce an anomalous pattern of emissions from areas of structural weakness by changing the stress levels within the structure.

While the invention has been described with reference to specific embodiments, modifications and variations of the invention may be constructed without departing from the scope of the invention, which is defined in the following claims.

We claim:

1. A system for testing integrity of civil structures for impending structural failure comprising plural sensors installed at spaced locations in the structures for picking up sounds of events indicative of impending structural failure, signal processors connected to the sensors for differentiating the sounds from background noise, memories in the signal processors for recording the sounds in the memories, timers in the signal processors and the memories for recording precise times of the sounds, and outputs connected to the memories for eventual downloading of recorded information.

2. The system in claim 1, further comprising a portable collector for connecting to the outputs and collecting recorded information of sounds and recorded times.

3. The system in claim 2, wherein the plural sensors comprise at least two sensors, and further comprising a central processor for connecting to the portable collector for downloading the recorded times and sounds from each memory into the central processor for analyzing the sounds and times from the at least two sensors for noting and localizing the events.

4. The system of claim 1, wherein the sensors comprise noise-cancelling sensors.

5. The system of claim 1, wherein the signal processors comprise noise filters.

6. The system of claim 5, wherein the noise filters comprise high band pass and low band pass filters.

7. The system of claim 6, further comprising acoustic signal detectors for detecting acoustic signals relevant to pipeline reinforcement breakage or slippage in the signal processors and wherein the timers are connected to the memories and the detectors.

8. The system of claim 7, further comprising GPS receivers connected to the signal processors for providing and receiving recorded information on locations of the sensors and signal processors, and for providing precise times of detection of the sounds.

9. The system of claim 1, wherein the sensors, signal processors, and outputs are connected in autonomous units, each unit having a sensor, a signal processor, and an output for positioning the units at spaced locations along the structure.

10. The system of claim 1, wherein the structure comprises a pipeline and the sensors comprise hydrophones disposed within fluid in the pipeline.

11. The system of claim 1, wherein the outputs comprise transmitters for transmitting signals containing information stored in the signal processors.

12. The system of claim 11, wherein the transmitters comprise transceivers for transmitting the information-containing signals in response to query signals from a collector communicating with the system.

13. The system of claim 1, further comprising pre-amplifiers connected to the sensors and to the signal processors for pre-amplifying signals from the sensors.

14. A system for non destructive testing of a prestressed structure, comprising plural autonomous units for positioning at spaced locations on the structure, each unit further comprising a sensor disposed within the structure for picking up events that may be associated with subsequent structural damage, a pre-amplifier connected to the sensor for pre-amplifying signals from the sensor, a signal processor connected to the pre-amplifier for differentiating signals of events from signals of background noise, a memory in the signal processor for recording signals of the events in the memory, a GPS receiver communicating with the processor for providing and receiving precise times of event signals, an output connected to the signal processor for eventual downloading of recorded information, and a source of power connected to the signal processor and the GPS receiver for providing power thereto, and the system further comprising a collector for collecting recorded information of event signals and times.

15. The system in claim 14, wherein the collector further comprises a portable hard drive.

16. The system of claim 15, further comprising a central processor for connecting to the collector for downloading the event signals and times from each memory into the central processor and analyzing the event signals and times from at least two units for noting and localizing structural defects.

17. The system of claim 14, wherein the sensors comprise noise-cancelling sensors.

18. The system of claim 14, wherein the signal processors comprise noise filters.

19. The system of claim 18, wherein the noise filters comprise high band pass and low band pass filters.

20. The system of claim 14, wherein the outputs comprise transmitters for transmitting signals containing information stored in the memories.

21. The system of claim 20, wherein the transmitters comprise transceivers for transmitting the information-containing signals in response to query signals from a collector communicating with the system.

22. A system for non destructive testing of a prestressed concrete cylinder pipeline, comprising plural autonomous units for positioning at spaced locations on the pipeline, each unit further comprising sensors for sensing fluid velocity, fluid temperature, fluid pressure, and a hydrophone disposed within fluid in the pipeline for detecting structural damage and fluid leaks and for picking up events that may be associated with subsequent structural damage, a pre-amplifier electrically connected to the sensor for pre-amplifying signals from the sensor, a signal processor connected to the pre-amplifier for differentiating event signals from signals of background noise, a GPS receiver communicating with the processor for providing precise times of event signals, a recorder communicating with the signal processor for recording precise times of event signals, an output connected to the recorder for downloading stored information, and a source of power connected to the signal processor and the GPS receiver for providing power thereto, and the system further comprising a collector for collecting recorded information of event times from the recorder in each unit.

23. The system in claim 22, wherein the collector further comprises a portable hard drive.

24. The system of claim 22, further comprising a central processor for connecting to the collector for downloading the event times from each recorder into the central processor and analyzing the event times from at least two units for noting and localizing structural defects.

25. The system of claim 22, wherein the sensors comprise noise-cancelling sensors.

26. The system of claim 22, wherein the signal processors comprise noise filters.

27. The system of claim 22, wherein the signal processors comprise high band pass and low band pass filters.

28. The system of claim 22, wherein the outputs comprise transmitters for transmitting signals from the signal processors containing information stored in the memories.

29. The system of claim 28, wherein the transmitters comprise transceivers for transmitting the information-containing signals in response to query signals from a collector communicating with the system.

30. A system for nondestructive testing of a prestressed concrete cylinder pipe structure, comprising plural autonomous units for positioning at spaced locations on the structure, each unit further comprising a sensor for picking up events that may be associated with subsequent structural damage, a pre-amplifier electrically connected to the sensor for pre-amplifying signals from the sensor, a signal processor connected to the pre-amplifier for differentiating even signals from signals of background noise, a GPS receiver communicating with the processor for providing precise times of event signals, a recorder communicating with the signal processor for recording precise times of event signals and the event signals, an output connected to the recorder for downloading stored information, and a source of power connected to the signal processor and the GPS receiver for providing power thereto, and the system further comprising a collector for collecting recorded information of event times and event signals from the recorder in each unit.

31. The system of claim 30, wherein each unit comprises sensors for sensing fluid velocity, fluid temperature, fluid pressure, and a hydrophone disposed within the fluid in the pipeline for detecting structural damage and fluid leaks.

* * * * *